United States Patent [19]
Nabi et al.

[11] Patent Number: 5,976,508
[45] Date of Patent: *Nov. 2, 1999

[54] METHOD TO ENHANCE THE ANTIBACTERIAL EFFICACY OF ANTIBACTERIAL DENTIFRICES

[75] Inventors: Nuran Nabi, Cranbury; John Afflitto, Brookside; Malcolm Williams, Piscataway; Susan Herles, Flemington; Prem Sreenivasan, Piscataway, all of N.J.

[73] Assignee: Colgate-Palmolive Company, New York, N.Y.

[ * ] Notice: This patent is subject to a terminal disclaimer.

[21] Appl. No.: 08/943,821

[22] Filed: Oct. 6, 1997

[51] Int. Cl.⁶ ................. A61K 7/16; A61K 7/20
[52] U.S. Cl. ................................. 424/53; 424/49
[58] Field of Search ........................... 424/49–88

[56] References Cited

U.S. PATENT DOCUMENTS 4,022,880  5/1977  Vinson et al. ............... 424/49
5,766,574  6/1998  Beck et al. ................... 424/53

FOREIGN PATENT DOCUMENTS

WO 97 21419  6/1997  WIPO .

*Primary Examiner*—Shep Rose
*Attorney, Agent, or Firm*—Henry S. Goldfine

[57] ABSTRACT

A method for enhancing the antiplaque efficacy of an antibacterial dentifrice, comprising preparing a multicomponent dentifrice composition having a first dentifrice component containing an antibacterial agent and manganese coordination complex compound, and a second dentifrice component containing a peroxide compound; maintaining the first and second dentifrice components separately prior to use; combining the dentifrice components and applying the two components to the teeth and periodontium, whereby the dentifrice provides enhanced inhibition of plaque growth.

8 Claims, No Drawings

METHOD TO ENHANCE THE ANTIBACTERIAL EFFICACY OF ANTIBACTERIAL DENTIFRICES

BACKGROUND OF THE INVENTION

1. Field of the Invention

The present invention relates to a two component dentifrice composition, having a first component containing an antibacterial agent and a manganese coordination complex compound, and a second component containing a peroxide compound and more particularly to such a composition which exhibits enhanced reduction of plaque growth.

2. The Prior Art

Plaque induced diseases, including periodontitis and gingivitis, are believed to involve anerobic bacterial infections. Periodontal disease affects the periodontium, which is the investing and supporting tissue surrounding a tooth (i.e. the periodontal ligament, the gingiva, and the alveolar bone). Gingivitis and periodontitis are inflammatory disorders of the gingiva and the periodontal ligament, respectively. Gingivosis and periodontosis are more severe conditions involving degenerative disorders of the tissue. Combinations of inflammatory and degenerative conditions are termed periodontitis complex.

Periodontal disease is a major cause of tooth loss in adults. Tooth loss from periodontal disease is a significant problem beginning at about age 35, but even by age 15, it is estimated that about 4 of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

The use of noncationic, water-insoluble antibacterial agents in oral products is disclosed in a number of references. One such reference is U.S. Pat. No. 4,022,889 which discloses compositions containing zinc salts and antibacterial agents such as halogenated salicylanilides and halogenated hydroxydiphenyl ethers. A particular halogenated diphenyl ether, triclosan or 2',4,4'-trichloro-2-hydroxydiphenyl ether, is disclosed in U.S. Pat. Nos. 5,178,851, 5,192,530 and 5,288,480 as a particularly effective antiplaque agent, especially as it is compatible with anionic components generally used in oral compositions.

The use of peroxide compounds is known in the dentifrice art. As disclosed in U.S. Pat. No. 5,614,174, peroxide compounds have been utilized in dentifrice formulations as adjuvants for cosmetic purposes such as tooth whitening which results from bleaching and cleansing of the tooth surfaces. Further, it is disclosed in U.S. Pat. No. 5,614,174, that various other materials may be included within such peroxide dentifrices, including antibacterial agents such as triclosan.

Manganese coordination complex gluconate compounds, such as manganese gluconate, are disclosed in U.S. Pat. No. 5,648,064 for the purpose of activating a peroxygen compound therein to provide an oral composition having an enhanced whitening effect. U.S. Pat. No. 5,648,064 encompasses a two component dentifrice composition having a first component containing a peroxygen compound and a second component containing a manganese coordination complex, and wherein other materials may be incorporated such as triclosan, as an antibacterial agent.

Considering the prevalence of periodontal disease, there is an ongoing need for improved, more effective agents that inhibit plaque growth to maximize the reduction of oral decay and disease associated with plaque formation.

SUMMARY OF THE INVENTION

The present invention encompasses a method of enhancing the antiplaque efficacy of dentifrices, comprising the application to the tooth and the periodontium of a two component dentifrice composition, having a first dentifrice component containing an antibacterial agent and a manganese coordination complex compound, and a second dentifrice component containing a peroxide compound; the first and second dentifrice components being separated prior to use, wherein when combined upon application to the teeth and periodontium the dentifrice unexpectedly provides enhanced reduction of plaque growth thereon, as will be hereinafter demonstrated.

DESCRIPTION OF THE PREFERRED EMBODIMENTS

In use, the components of the two component dentifrice of the present invention comprise a first antibacterial agent and manganese coordination complex compound containing dentifrice component, and a second peroxide compound containing dentifrice component which are preferably combined in approximately equal weight proportions, so that only about one-half of the concentration of any particular ingredient within either component will be present when the components are combined and applied to the teeth and the periodontium, as by brushing. Both components are formulated to provide similar apparent physical characteristics, to promote similar rheology, so that the two components are delivered in the desired equal measure by extrusion from a multicompartmented tube or pump device.

Dentifrice Vehicle Common to Both Components

In the preparation of both dentifrice components of the present invention, the respective antibacterial agent/manganese coordination complex compound or peroxide compound is incorporated within a dentifrice vehicle suitable for use in the oral cavity, which contains water, humectant, surfactant and a polishing agent or abrasive. The humectant is generally a mixture of humectants, such as glycerol, sorbitol and polyethylene glycol of a molecular weight in the range of 200–1000, but other mixtures of humectants and single humectants may also be employed. The humectant content within each of the two components is in the range about of 20% to about 50% by weight and preferably about 30 to about 45% by weight. The water content is from about 8% to about 30%, and preferably about 12 to about 22% by weight.

Surface active agents or surfactants may be incorporated in the vehicle of both components of the present invention, as an ingredient to aid in the thorough dispersion of the dentifrice throughout the oral cavity when applied thereto, as well as, to improve the dentifrice's cosmetic acceptability and the foaming properties. Useful surface active agents include anionic, nonionic or ampholytic compounds, anionic compounds being preferred. Examples of suitable surfactants include salts of the higher alkyl sulfates, such as sodium lauryl sulfate or other suitable alkyl sulfates having 8 to 18 carbon atoms in the alkyl group; sodium lauryl sulfoacetate, salts of sulfonated monoglycerides of higher fatty acids, such as sodium coconut monoglyceride sulfonate or other suitable sulfonated monoglycerides of fatty acids of 10 to 18 carbon atoms; salts of amides of higher fatty acid, e.g., 12 to 16 carbon atom acids, with lower aliphatic amino acids, such as sodium-N-methyl-N-palmitoyl tauride, sodium N-lauroyl-, N-myristoyl- and N-palmitoyl sarcosinates; salts of the esters of such fatty acids with isotonic acid or with glycerol monosulfate, such as the sodium salt of monosulfated monoglyceride of hydrogenated coconut oil fatty acids; salts of olefin sulfonates, e.g. alkene sulfonates or alkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium, potassium or mono-, di or triethanol amine.

The surface active agent can be present in one or both components of the compositions of the present invention, at a concentration of about 0.5 to about 5.0% by weight, preferably about 1 to about 2% by weight of the particular component.

Useful dentifrice polishing agents or abrasives for incorporation into the dentifrice component vehicles include sodium metaphosphate, potassium metaphosphate, tricalcium phosphate, dihydrated dicalcium phosphate, aluminum silicate, calcined alumina, bentonite or siliceous materials or combinations thereof. It is important to note that certain polishing agents or abrasives may chemically interact and effect the stability of the peroxide compound within the second peroxide containing dentifrice component. A preferred class of polishing agents, which does not interact with peroxide compounds are siliceous materials, such as silica, which have a mean particle size up to about 20 microns; including a precipitated amorphous hydrated silica, such as Zeodent 115, marketed by J. M. Huber Chemicals Division, Havre de Grace, Md. 21078, or Sylodent 783 marketed by Grace Davidson, Baltimore, Md. 21203.

Such a silica polishing agent is present in each of the two dentifrice components of the present invention, at a concentration from about 10 to about 30% by weight, and preferably 15 to about 25% by weight of the respective component.

Antibacterial Agent & Manganese Coordination Complex Component

The first, antibacterial agent and manganese coordination complex containing dentifrice component, contains 0.2 to 1.0 percent by weight of an antibacterial agent, including non-cationic antibacterial agents which are based on phenolic or bisphenolic compounds, such as a halogenated diphenyl ethers like triclosan (2,2'-dihydroxy-5,5'-dibromodiphenyl ether), benzoate esters or carbanilides. A preferred antibacterial agent is triclosan, which is a broad-spectrum antibacterial agent, marketed for use in oral products under the tradenames Irgacare MP or Irgasan DP300 by Ciba-Geigy Corporation, Greensboro, N.C. 27419.

A manganese coordination complex compound is an essential ingredient in the first dentifrice component of this invention. From about 0.05 to about 1.5% by weight of such manganese coordination complex compounds should be present in the first dentifrice component, preferably from about 0.08 to about 0.12%. Such manganese coordination complex compounds include a complex of manganese (III) and a multidentate ligand supplied by a complexing agent, such compounds are known as activator compounds in the art and are more fully described in U.S. Pat. No. 5,648,064,  the disclosure of which is incorporated herein by reference. Preferred activators, in accordance with the practice of the present invention, include a complex of manganese (III) and a multidentate ligand supplied by a hydroxy carboxylic acid complexing agent containing at least 5 carbon atoms including hexonic hydroxy acids such as gluconic acid, gulonic acid, idonic acids such as glucouronic acid, galactouronic acid and mannuronic acid, heptonic hydroxy acids such as glucoheptanoic acid and sugars such as saccharic acid and isosaccharic acid. A most preferred manganese coordination complex compound is Mn (III) gluconate, which is available from Rhone-Poulenc, Cranbury, N.J. 08512.

Other useful manganese coordination complex compounds suitable for use in the practice of the present invention include manganese complexes of the formula:

wherein: M is manganese in the +3 or +4 oxidation state; n and m are integers from 1 to 4; X represents a coordination or a bridging species that coordinates with the manganese and is selected from $H_2O$, $OH^-$, $O_2^-$, $SH^-$, and alkyl and aryl groups having 1 to 20 carbon atoms and L is a ligand having at least 2 nitrogen, phosphorus, oxygen or sulfur atoms coordinating with the manganese.

Examples of ligands suitable for the formation of the manganese complexes of the formula are more fully described in U.S. Pat. No. 5,194,416, such description being incorporated herein by reference. Preferred examples of such ligands, L in the formula above, include: 1,4,7-triazacyclononane, 1,4,7-triazacyclodecane, 1,4,8-triazacycloundecane, 1,5,9-triazacyclodecane, 1,4,7-trimethyl-1,4,7-triazacyclononane, 1,4,7-trimethyl-1,4,7-triazacyclodecane, 1,4,8-trimethyl-1,4,8-triazacycloundecane, 1,5,9-trimethyl-1,5,9-triazacyclododecane, tris(pyridin-2-yl) methane, tris(pyrazol-1-yl) methane, tris(imidazol-2-yl) methane, tris(pyridin-2-yl) borate, tris (imidazol-2-yl) phosphine, 1,1,1-tris (methylamino) ethane, Bis(pyridin-2-yl-methyl)amine, Bis(triazol-1-yl-methyl)amine and Bis(imidazol-2-yl-methyl)amine.

An antibacterial-enhancing agent (AEA) such as those disclosed in U.S. Pat. No. 5,288,480 which enhances the delivery and retention of the antibacterial agent to, and retention thereof on oral surfaces is preferably included in the first dentifrice component. The proportion of AEA in this first dentifrice component can be from about 15 to about 30% by weight. AEA's useful in the present invention include synthetic anionic polymeric polycarboxylates, in the form 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez, e.g. AN 139 (M.W. 500,000), AN 119 (M.W. 250,000) and preferably S-97 Pharmaceutical Grade (M.W. 700,000) available from ISP Technologies, Inc., Bound Brook, N.J. 08805.

A basic buffering agent may be required to balance the acidity introduced into this first dentifrice component by the AEA, to a pH range which is preferably from about 6.5 to about 7.5. A preferred buffering agent is a 50% aqueous solution of sodium hydroxide, whose proportion within the first dentifrice component may vary from about 1.5 to about 3% in order to obtain the desired neutral pH.

Peroxide Containing Component

The second, peroxide compound containing component of the dentifrice composition of the present invention is maintained physically separate from the first component prior to extrusion from a multicompartmented tube or pump in which it may be stored prior to use. The presence of such oxidizing compounds can vary from about 0.1 to about 5% by weight of the second component, preferably about 4%; wherein such oxidizing agents include peroxygen compounds. Particularly useful peroxygen compounds include hydrogen peroxide, peroxydiphosphate, urea peroxide, metal peroxides such as calcium peroxide, sodium peroxide, stronthium peroxide, magnesium peroxide, and the salts of perborate, persilicate, perphosphate and percarbonate such as sodium perborate, potassium persilicate and sodium percarbonate. The most suitable and preferred peroxygen compound for this invention is hydrogen peroxide.

An antioxidant may be incorporated into the second peroxygen containing dentifrice component, such as butylated hydroxytoluene (BHT) or di-t-butyl hydroquinone (BHA), to add chemical stability to the component. Such antioxidants, where present, are incorporated in the preparations of the subject invention in amounts which do not substantially adversely affect the properties and characteristics desired.

Certain antitartar toothpaste ingredients are not chemically compatible with noncationic antibacterial agents such as triclosan and hence must, if present, be included in the second dentifrice component of the toothpaste of the present invention; such anti-tartar ingredients include sodium tripolyphosphate, tetrasodium pyrophosphate and sodium acid pyrophosphate. These antitartar ingredients may be present individually or in combination, from about 4 to about 10% by weight of this second component.

Other Ingredients Common to Both Components

Inorganic or organic thickeners may be included in the both of the components of the dentifrice of the present invention. Organic thickeners such as natural and synthetic gums and colloids may also be incorporated in the present invention. Examples of such organic thickeners include carrageenan (Irish moss), xanthan gum and sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Inorganic thickeners are preferred, include amorphous silica compounds which function as thickening agents include, colloidal silicas compounds available under tradenames such as Cab-o-sil fumed silica manufactured by Cabot Corporation and distributed by Lenape Chemical, Bound Brook, N.J., Zeodent 165 from J. M. Huber Chemicals Division, Havre de Grace, Md. 21078, and Sylox 15 from Grace Davidson, Baltimore, Md. 21203. Either inorganic or organic thickening agents, or combinations thereof, may be present in both components of the instant dentifrice in proportions of about 0.1 to about 5% by weight, preferably about 0.4 to about 3% in each of the two dentifrice components.

A striped dentifrice product may be obtained using the multicomponent dentifrice of the present invention, wherein colorants of contrasting colors are incorporated in each of the dentifrice components to be dispensed; the colorants being pharmacologically and physiologically non-toxic when used in the suggested amounts. Colorants used in the practice of the present invention include both pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The concentration of the dye in the dentifrice composition in an amount from about 0.0005 percent to about 2 percent by weight of the respective component.

A water-soluble anticaries fluoride ion releasing compound, can be contained in either or both of the dentifrice components of the present invention. The fluoride compound may be in an amount sufficient to give a fluoride ion concentration in the composition at 25° C., and/or when it is used of from about 0.0025% (25 ppm) to about 4% (40,000 ppm) by weight, preferably from about 0.005% (50 ppm) to about 2% (20,000 ppm) by weight, to provide additional anticaries effectiveness. Examples of suitable fluoride ion releasing compounds include: sodium fluoride, potassium fluoride, sodium monofluorophosphate, sodium hexafluorosilicate among others. Sodium monofluorophosphate and sodium fluoride are particularly preferred, as well as mixtures thereof.

Other ingredients which may be incorporated in one or both components of the present invention, include sweetener, flavor and preservative. The sweetener content will normally be that of an artificial or synthetic sweetener and the normal proportion thereof present will be in the range of 0.1 to 1% by weight of the respective component, preferably 0.2 to 0.5% by weight the respective component. The flavor content, which is preferably of a mixed peppermint/menthol flavor, will usually be in the range of 0.5 to 2% by weight of the respective component, preferably 0.5 to 1.0% by weight of the respective component. The contents of other components or adjuvants will normally not exceed 10% by weight, often will be less than 5% by weight, and can be as low as 0%.

Preparation of the Dentifrice

To prepare the peroxygen second component of the present invention, generally the humectants e.g. glycerin, propylene glycol, polyethylene glycol ingredients, are dispersed with any sweetener and water in a conventional mixer, until the mixture becomes a homogeneous gel phase. Into the gel phase are added a pigment such as $TiO_2$ and any tartar control agents such as tetrasodium pyrophosphate or sodium tripolyphosphate or both and any fluoride anticaries agents, such as sodium fluoride. These ingredients are mixed until a homogenous phase is obtained. Thereafter the thickener, peroxide compound, flavor and surfactant ingredients are added and the ingredients mixed at high speed under vacuum of from about 20 to 100 mm of Hg. The resultant product is in each case a homogeneous, semi-solid, extrudable paste product.

To prepare the antibacterial/manganese coordination complex containing first component of the dentifrice of the present invention, the procedure is generally the same as that described above for the peroxide containing second dentifrice component; except that the antibacterial agent, the manganese coordination complex compound such as manganese gluconate, any pH buffering solution such as sodium hydroxide and the dye ingredients are incorporated in the initial mixture of humectants and sweetener, the polishing agent/abrasive is mixed into the gel phase prior to adding the AEA such as Gantrex S-97 with the thickener such as gum, Sylodent 15 or sodium carboxymethyl cellulose.

Packaging of the Dentifrice

The two component dentifrice composition of the present invention is packaged in a suitable dispensing container in which the components are maintained physically separated and from which the separated components may be dispensed synchronously as a ribbon for application to a toothbrush.

Such containers are known in the art. An example of such a container is a two compartment dispensing container having collapsible sidewalls, as disclosed in U.S. Pat. Nos. 4,487,757 and 4,687,663 wherein the container body is formed from a collapsible plastic web and is provided with a partition within the container body defining separate compartments in which the physically separated components are stored and from which they are dispensed through a suitable dispensing outlet.

The following example is further illustrative of the present invention, but it are understood that the invention is not limited thereto. All amounts and proportions referred to herein and the appended claims are by weight.

EXAMPLE

The antiplaque activity of a two component dentifrice formulation of the present invention, Dentifrice A, was assessed using a chemostat plaque model system of the type disclosed in the American Journal of Dentistry, Vol. 3, pages S8–S9 (1990). The formulation of each component of Dentifrice A is presented in Table I, below. The chemostat plaque model simulates the actual saliva and tooth surface interactions with respect to the plaque formation in the mouth and assesses the interactions, at the biophysical and surface chemical levels, of saliva-coated bacteria to saliva-coated surfaces with a surface energy similar to dental enamel. Prior to application to the experimental saliva-coated surface, the two components of Dentifrice A were maintained and stored separately in a dual chamber tube to avoid any interaction between the relatively reactive and unstable peroxide compound and other ingredients of the dentifrice, especially such reactions affecting the peroxide itself, as well as, the antibacterial agent, the AEA and certain flavors and coloring agents.

TABLE I

Dentifrice A
A Two Component Dentifrice of the Present Invention

| Ingredients | Component 1 | Component 2 |
|---|---|---|
| Glycerin | 20.0 | 20.0 |
| Zeodent 115 | 20.0 | 25.0 |
| Polyethylene Glycol-600 | — | 5.0 |
| Sorbitol 70% | 15.0 | 20.0 |
| Sylodent 15 | 1.5 | — |
| Tetrasodium Pyrophosphate | — | 4.0 |
| Sodium Acid Pyrophosphate | — | 4.0 |
| Titanium Dioxide | 0.5 | — |
| Cellulose Gum | 0.4 | 0.4 |
| Sodium CMC | 0.8 | — |
| Flavor Oil | 1.0 | 0.8 |
| Sodium Saccharin | 0.6 | 0.5 |
| Potassium Stannate | — | 0.5 |
| Triclosan | 0.6 | — |
| Gantrez S-97 (13.6% liq.) | 15.0 | — |
| Sodium Hydroxide (50% solution) | 2.4 | — |
| Sodium Lauryl Sulfate | 1.5 | 0.8 |
| Hydrogen Peroxide | — | 4.0 |
| Manganese Gluconate | 0.1 | — |
| Sodium Fluoride | 0.486 | — |
| BHT | — | 0.03 |
| Water | 20.114 | 14.97 |
| Totals | 100.00 | 100.00 |

The chemostat consists of a source of bacterial growth media contained in a mixing chamber (Bioflo, Model C32, available from New Brunswick Scientific Co., Inc., Edison, N.J.) and flow cells connected thereto. Hydroxyapatite (HAP) disks are fixed in the flow cells, providing the dental enamel like surface to support the plaque growth. The HAP disks are prepared by grinding 150 mgs. of dried hydroxyapatite into a powder with a mortar and pestle; forming this powder with a KBr pellet die (Barnes Analytical, Stanford, Conn.) and compressing the formed powder under 10,000 pounds pressure for 6 minutes in a Carver Laboratory press onto 12 mm diameter, 1 mm thick stamped metal disks. The resulting HAP disks are sintered for 4 hours at 800° C. in a Thermolyne furnace.

Whole saliva, supplemented with trypticase soy broth (TSB; Becton Dickinson and Company, Cockeysville, Md.), was circulated through the flow system, over the HAP disks, at a flow rate of 1 mL/minute. Circulation was done for up to 72 hours, with TSB-saliva changes every 24 hours. All saliva changes and treatments were done without disassembling the flow cell system or allowing the plates to go dry.

To assess the anti-plaque efficacy of Dentifrice A, the two components of Dentifrice A were combined and immediately diluted in a separate reservoir with three parts ambient temperature water to each part of the combined two component dentifrice. The separate reservoir was then connected to the flow cells, which were pulsed at a flow rate of 10 mL/minute, for 30 second intervals, with the 3:1 diluted aqueous solution of Dentifrice A from the reservoir. This exposure of the flow cells to Dentifrice A was carried out once each 24 hour period for 30 minutes (saliva single pass through) before the TBS-saliva circulation was resumed.

After 72 hours, the pumps were stopped and the recirculating systems were disconnected from the saliva dispensers. The flow cells were then rinsed with deionized water (single pass through) for 20 minutes to remove any loosely bound materials. The flow system was then disassembled and the test plates were air dried overnight in a vertical position before analysis.

After drying, the plates were analyzed using Attenuated Total Reflectance Furrier Transform Infrared Spectrophotometry (ATR-FTIR). Scanning was done at a scan rate of $0.2$ cm.s$^{-1}$ and a resolution of 4 cm$^{-1}$. A plaque score (P.S.) was calculated, using the maximum absorption bands at 3300, 1650, 1540, and 1080 cm$^{-1}$ (from the infrared spectrum). The plaque index was calculated as follows:

$$P.S.=[A(3300)]+[A(1650)]+[A(1540)]+[A(1080)]$$

where: A is the maximum absorbance at the various wave numbers. The wave numbers selected reflect the absorption of salivary components to and the growth of bacteria on germanium prisms. The lower the plaque score, the lower plaque accumulation detected and the greater the antiplaque efficacy of the particular dentifrice. The plaque score for Dentifrice A is presented in Table II, below.

For comparison purposes, the procedure of the Example was repeated a series of times with the formulation of the Example; in each case with extra water added and the following ingredients) removed therefrom in whole or part: (1) the manganese gluconate was removed (Dentifrice B); (2) the manganese gluconate was removed and the quantity of H$_2$O$_2$ was reduced to 1.25% from 2% (Dentifrice C); and (3) all of the manganese gluconate and the H$_2$O$_2$ was removed (Dentifrice D). The plaque scores for comparative Dentifrices B, C and D are also presented in Table II, below.

TABLE II

Plaque Scores of Dentifrice A and Comparatives B, C and D

| | Dentifrice Tested | Plaque Score (Standard Deviation) |
|---|---|---|
| A. | (0.3% triclosan, 0.05% Mn gluconate, 2.0% $H_2O_2$) | 0.52 +/− 0.05 |
| B. | (0.3% triclosan, 2.0% $H_2O_2$) | 0.71 +/− 0.03 |
| C. | (0.3% triclosan, 1.25% $H_2O_2$) | 1.07 +/− 0.04 |
| D. | (0.3% triclosan) | 1.16 +/− 0.09 |

Referring to Table II, the plaque score for Dentifrice A, of the present invention, showed an unexpected reduction in plaque growth (i.e. enhanced inhibition of plaque formation) of over 55% compared to Dentifrice D, containing only triclosan. The plaque scores for Dentifrices B and C, containing triclosan and varying quantities of $H_2O_2$, while statistically different and better than Dentifrice D were not as efficacious as Dentifrice A, in which were present the three critical elements of the present invention: triclosan, $H_2O_2$, and manganese gluconate.

What is claimed is:

1. A method for enhancing the antiplaque efficacy of antibacterial containing dentifrices comprising, preparing a two component dentifrice composition having a first dentifrice component containing an antibacterial agent, a silica abrasive, and a manganese coordination complex, and a second dentifrice component containing a peroxide compound and a silica abrasive; maintaining the first and second dentifrice components physically separated prior to use; applying the two dentifrice components such that when combined upon application to the teeth and periodontium, the dentifrice provides enhanced inhibition of plaque growth.

2. The method of claim 1, wherein the antibacterial agent is a non-cationic halogenated diphenyl ether.

3. The method of claim 2, wherein the non-cationic halogenated diphenyl ether is triclosan.

4. The method of claim 1, wherein the manganese coordination complex is Mn (III) gluconate.

5. The method of claim 1, wherein the peroxide compound is hydrogen peroxide.

6. The method of claim 1, wherein the quantity of antibacterial agent is from about 0.2 to about 1.0 percent by weight of the first dentifrice component.

7. The method of claim 1, wherein the manganese coordination complex compound is from about 0.05 to about 1.5 percent by weight of the first dentifrice component.

8. The method of claim 1, wherein the peroxide compound is from about 0.1 to about 5 percent by weight of the second dentifrice component.

* * * * *